(12) United States Patent
Bosua

(10) Patent No.: US 11,033,208 B1
(45) Date of Patent: Jun. 15, 2021

(54) FIXED OPERATION TIME FREQUENCY SWEEPS FOR AN ANALYTE SENSOR

(71) Applicant: Know Labs, Inc., Seattle, WA (US)

(72) Inventor: Phillip Bosua, Seattle, WA (US)

(73) Assignee: KNOW LABS, INC., Seattle, WA (US)

( * ) Notice: Subject to any disclaimer, the term of this patent is extended or adjusted under 35 U.S.C. 154(b) by 0 days.

(21) Appl. No.: 17/168,788

(22) Filed: Feb. 5, 2021

(51) Int. Cl.
*A61B 5/05* (2021.01)
*A61B 5/145* (2006.01)
(Continued)

(52) U.S. Cl.
CPC .......... *A61B 5/1455* (2013.01); *A61B 5/0507* (2013.01); *A61B 5/14532* (2013.01); *A61B 5/14546* (2013.01); *A61B 5/4845* (2013.01); *A61B 10/0012* (2013.01); *G01N 21/25* (2013.01); *G01N 22/00* (2013.01); *G01N 33/49* (2013.01); *A61B 5/681* (2013.01); *A61B 5/6891* (2013.01); *A61B 2562/0228* (2013.01); *A61B 2562/0233* (2013.01); *G01N 2201/062* (2013.01)

(58) Field of Classification Search
CPC ..... A61B 5/05; A61B 5/1455; A61B 5/14551; A61B 5/14532; A61B 5/4845; A61B 5/14546; A61B 5/0507; A61B 5/681; A61B 5/6891
See application file for complete search history.

(56) References Cited

U.S. PATENT DOCUMENTS 4,202,000 A 5/1980 Carballes
8,223,021 B2 7/2012 Goodnow et al.
(Continued)

FOREIGN PATENT DOCUMENTS

JP 2012125382 7/2012
KR 1020160081740 7/2016
(Continued)

OTHER PUBLICATIONS

Hanna, J. et al., "Noninvasive, wearable, and tunable electromagnetic multisensing system for continuous glucose monitoring, mimicking vasculature anatomy," Science Advances, 6, eaba5320, 2020 (11 pages).
(Continued)

*Primary Examiner* — Chu Chuan Liu
(74) *Attorney, Agent, or Firm* — Hamre, Schumann, Mueller & Larson, P.C.

(57) ABSTRACT

Sensors that detect an analyte via spectroscopic techniques using non-optical frequencies such as in the radio or microwave frequency range of the electromagnetic spectrum or optical frequencies in the visible range of the electromagnetic spectrum. An analyte sensor described herein includes a detector array having at least one transmit element and at least one receive element. The transmit element and the receive element can be antennas or light emitting elements such as light emitting diodes. The sensor is controlled to implement first and second frequency sweeps and the frequency sweeps have at least one overlapping range of frequencies where the operation times are the same between the first and second frequency sweeps.

14 Claims, 9 Drawing Sheets

(51) Int. Cl.
*A61B 5/1455* (2006.01)
*G01N 33/49* (2006.01)
*G01N 22/00* (2006.01)
*G01N 21/25* (2006.01)
*A61B 10/00* (2006.01)
*A61B 5/0507* (2021.01)
*A61B 5/00* (2006.01)

(56) References Cited

U.S. PATENT DOCUMENTS

| | | | |
|---|---|---|---|
| 8,882,670 B2 | 11/2014 | Hancock | |
| 9,198,607 B2 | 12/2015 | Fischer | |
| 9,864,024 B2 | 1/2018 | Vester | |
| 10,149,629 B2 | 12/2018 | Szczepaniak et al. | |
| 10,258,268 B2 * | 4/2019 | Roblyer | A61B 5/14551 |
| 10,478,101 B1 | 11/2019 | Cespedes et al. | |
| 10,548,503 B2 | 2/2020 | Bosua | |
| 2003/0036713 A1 | 2/2003 | Bouton et al. | |
| 2004/0065158 A1 | 4/2004 | Schrepfer et al. | |
| 2004/0127777 A1 | 7/2004 | Ruchti et al. | |
| 2004/0133086 A1 | 7/2004 | Ciurczak et al. | |
| 2009/0275814 A1 | 11/2009 | Watanabe et al. | |
| 2010/0041969 A1 | 2/2010 | Beise | |
| 2011/0028814 A1 | 2/2011 | Petersen et al. | |
| 2014/0213870 A1 | 7/2014 | Hsu et al. | |
| 2016/0051171 A1 | 2/2016 | Pikov et al. | |
| 2017/0095667 A1 | 4/2017 | Yakovlev et al. | |
| 2018/0028824 A1 | 2/2018 | Pivonka et al. | |
| 2019/0008422 A1 | 1/2019 | Leath et al. | |
| 2019/0053741 A1 | 2/2019 | Chaudhry | |
| 2019/0104939 A1 | 4/2019 | Costantine et al. | |
| 2019/0388000 A1 | 12/2019 | Costantine et al. | |
| 2020/0057163 A1 | 2/2020 | Bromberg | |
| 2020/0146584 A1 | 5/2020 | Bosua | |
| 2020/0187791 A1 | 6/2020 | Leabman | |
| 2020/0187792 A1 | 6/2020 | Leabman | |
| 2020/0187793 A1 | 6/2020 | Leabman | |
| 2020/0187812 A1 | 6/2020 | Leabman | |
| 2020/0187813 A1 | 6/2020 | Leabman | |
| 2020/0187814 A1 | 6/2020 | Leabman | |
| 2020/0187815 A1 | 6/2020 | Leabman | |
| 2020/0187816 A1 | 6/2020 | Leabman | |
| 2020/0187817 A1 | 6/2020 | Leabman | |
| 2020/0187818 A1 | 6/2020 | Leabman | |
| 2020/0187819 A1 | 6/2020 | Leabman | |
| 2020/0187820 A1 | 6/2020 | Leabman | |
| 2020/0187836 A1 | 6/2020 | Leabman | |
| 2020/0187837 A1 | 6/2020 | Leabman | |
| 2020/0187867 A1 | 6/2020 | Leabman | |
| 2020/0191909 A1 | 6/2020 | Leabman | |
| 2020/0191932 A1 | 6/2020 | Leabman | |
| 2020/0191933 A1 | 6/2020 | Leabman | |
| 2020/0191944 A1 | 6/2020 | Leabman | |
| 2020/0191945 A1 | 6/2020 | Leabman | |
| 2020/0191947 A1 | 6/2020 | Leabman | |
| 2020/0192426 A1 | 6/2020 | Leabman | |
| 2020/0192427 A1 | 6/2020 | Leabman | |
| 2020/0192428 A1 | 6/2020 | Leabman | |
| 2020/0193326 A1 | 6/2020 | Leabman | |
| 2020/0195197 A1 | 6/2020 | Leabman | |
| 2020/0195293 A1 | 6/2020 | Leabman | |

FOREIGN PATENT DOCUMENTS

| | | |
|---|---|---|
| WO | 2017163245 | 9/2017 |
| WO | 2019071138 | 4/2019 |
| WO | 2019217461 | 11/2019 |
| WO | 2020006077 | 1/2020 |
| WO | 2020037171 | 2/2020 |

OTHER PUBLICATIONS

"Contributes to longer healthy life expectancy with non-invasive vital acquisition sensor," Quantum Operation Co., Ltd., presentation found on Jan. 12, 2021 at https://oi.nttdata.com/program/forum/history/20191118/pdf/03_quantum-op.pdf (14 pages including English translation).

International Search Report and Written Opinion for PCT/US2019/031176, dated Aug. 23, 2019, 9 pages.

Qiang et al., "Quantitative detection of glucose level based on radiofrequency patch biosensor combined with volume-fixed structures," Biosensors and Bioelectronics 98:357-363, 2017.

Shaker, G. et al., "Non-Invasive Monitoring of Glucose Level Changes Utilizing a mm-Wave Radar System," IJMHCI, vol. 10, Issue 3 (2018): pp. 10-29.

Lien, J. et al., "Soli: Ubiquitous Gesture Sensing with Millimeter Wave Radar," ACM Trans. Graph., vol. 35, No. 4, Article 142, 19 pages (Jul. 2016).

Stojanovic, R. et al., "An optical sensing approach based on light emitting diodes," Journal of Physics: Conference Series 76 (2007), pp. 1-6.

Rossiter, J. et al., "A novel tactile sensor using a matrix of LEDs operating in both photoemitter and photodetector modes," Proc of 4th IEEE International Conference on Sensors (IEEE Sensors 2005), pp. 994-997.

U.S. Appl. No. 17/123,932, titled "Non-Invasive Analyte Sensor and System With Decoupled Transmit and Receive Antennas," filed Dec. 16, 2020 (49 pages).

U.S. Appl. No. 17/123,947, titled "Non-Invasive Detection of an Analyte Using Decoupled Transmit and Receive Antennas," filed Dec. 16, 2020 (46 pages).

U.S. Appl. No. 17/123,961, titled "Non-Invasive Analyte Sensor and System With Decoupled and Inefficient Transmit and Receive Antennas," filed Dec. 16, 2020 (48 pages).

U.S. Appl. No. 17/123,977, titled "Non-Invasive Detection of an Analyte Using Decoupled and Inefficient Transmit and Receive Antennas," filed Dec. 16, 2020 (47 pages).

U.S. Appl. No. 17/123,992, titled "Non-Invasive Analyte Sensor Device," filed Dec. 16, 2020 (47 pages).

U.S. Appl. No. 17/164,073, titled "Analyte Sensor and System With Multiple Detector Elements That Can Transmit or Receive," filed Feb. 1, 2021 (65 pages).

U.S. Appl. No. 17/164,086, titled "Detection of an Analyte Using Multiple Elements That Can Transmit or Receive," filed Feb. 1, 2021 (65 pages).

U.S. Appl. No. 17/164,103, titled "Detection of an Analyte Using Different Combinations of Detector Elements That Can Transmit or Receive," filed Feb. 1, 2021 (65 pages).

U.S. Appl. No. 17/171,279, titled "Non-Invasive Detection of an Analyte and Notification of Results," filed Feb. 9, 2021 (49 pages).

U.S. Appl. No. 17/171,281, titled "Non-Invasive Analyte Sensing and Notification System With Decoupled Transmit and Receive Antennas," filed Feb. 9, 2021 (49 pages).

U.S. Appl. No. 17/171,284, titled "Non-Invasive Analyte Sensing and Notification System With Decoupled and Inefficient Transmit and Receive Antennas," filed Feb. 9, 2021 (49 pages).

* cited by examiner

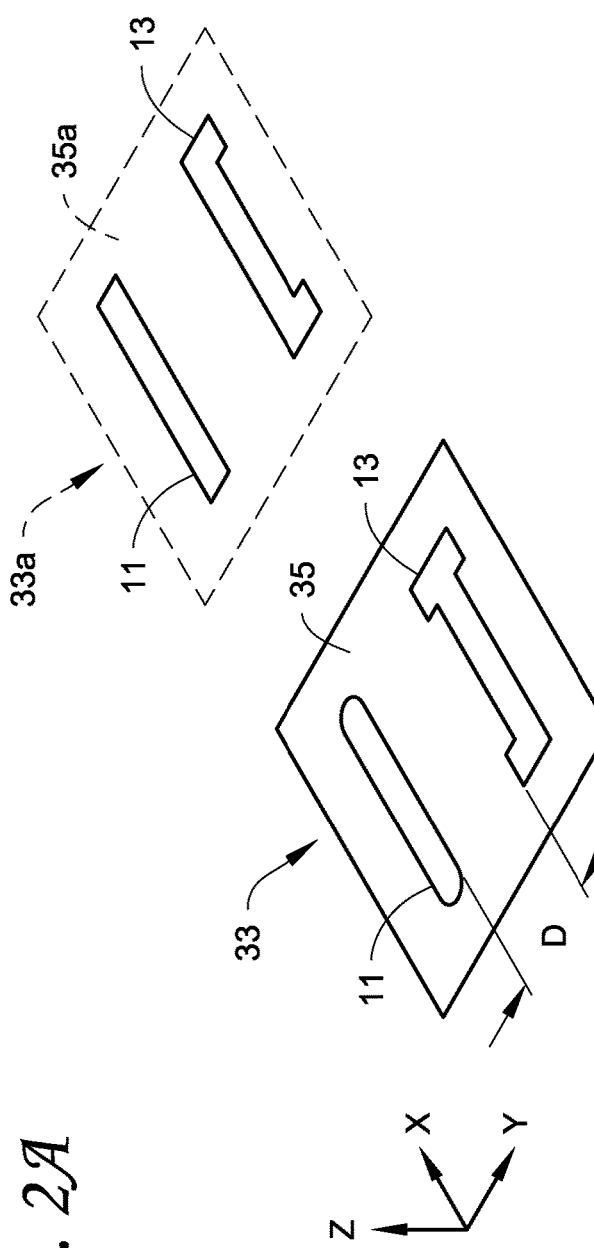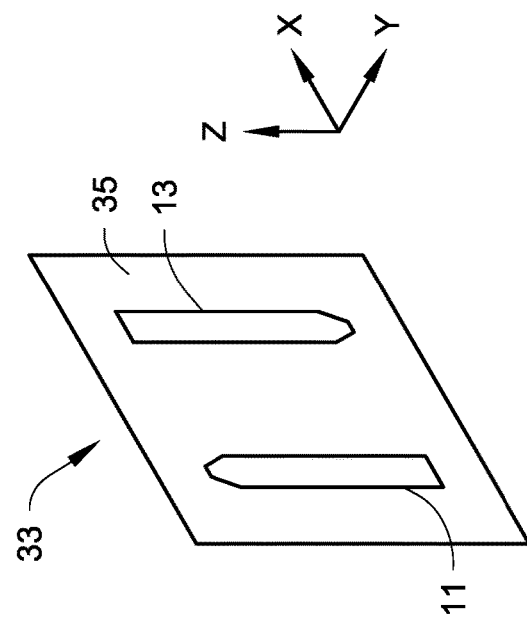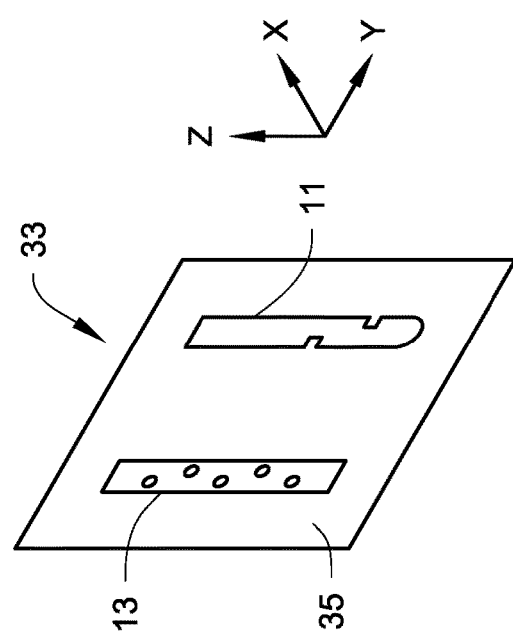

FIXED OPERATION TIME FREQUENCY SWEEPS FOR AN ANALYTE SENSOR

FIELD

This disclosure relates generally to apparatus, systems and methods of detecting an analyte via spectroscopic techniques using an analyte sensor that includes at least one transmit element and at least one receive element, where the transmit element and the receive element operate in the radio or microwave frequency range of the electromagnetic spectrum or operate in the visible range of the electromagnetic spectrum.

BACKGROUND

There is interest in being able to detect and/or measure an analyte within a target. One example is measuring glucose in biological tissue. In the example of measuring glucose in a patient, current analyte measurement methods are invasive in that they perform the measurement on a bodily fluid such as blood for fingerstick or laboratory-based tests, or on fluid that is drawn from the patient often using an invasive transcutaneous device. There are non-invasive methods that claim to be able to perform glucose measurements in biological tissues. However, many of the non-invasive methods generally suffer from: lack of specificity to the analyte of interest, such as glucose; interference from temperature fluctuations; interference from skin compounds (i.e. sweat) and pigments; and complexity of placement, i.e. the sensing device resides on multiple locations on the patient's body.

SUMMARY

This disclosure relates generally to apparatus, systems and methods of detecting an analyte via spectroscopic techniques using non-optical frequencies such as in the radio or microwave frequency range of the electromagnetic spectrum or optical frequencies in the visible range of the electromagnetic spectrum. An analyte sensor described herein includes a detector array having at least one transmit element and at least one receive element. The transmit element and the receive element can be antennas or light emitting elements such as light emitting diodes. In the following description, the transmit element and the receive element, whether they are antennas or light emitting diodes, may each be referred to as a detector element.

The transmit element is controlled so as to implement at least first and second frequency sweeps. Additional frequency sweeps can be implemented with each frequency sweep being like the first and second frequency sweeps. The first frequency sweep occurs over a first frequency range from a start frequency to an end frequency, and the second frequency sweep occurs over a second frequency range from a start frequency to an end frequency. In one embodiment, the first frequency range and the second frequency range at least partially overlap one another. In another embodiment, the first frequency range and the second frequency range are identical to one another. The first frequency range and the second frequency range where they overlap have first frequency steps and second frequency steps, respectively. In the overlapping range, the first frequency steps are the same as the second frequency steps. Each frequency step of the first frequency steps and the second frequency steps has an associated operation time, and the operation times of the first frequency steps of the first frequency range are identical to the operation times of the second frequency steps of the second frequency range. Because each the first and second frequency sweeps, at least where they overlap one another, are conducted substantially identically to one another, a more accurate comparison between the results of each frequency sweep can be conducted.

In one embodiment described herein, a sensor system can include a detector array having at least one transmit element and at least one receive element. The at least one transmit element is positioned and arranged to transmit a transmit signal into a target, and the at least one receive element is positioned and arranged to detect a response resulting from transmission of the transmit signal by the at least one transmit element into the target. A transmit circuit is electrically connectable to the at least one transmit element, where the transmit circuit is configured to generate the transmit signal to be transmitted by the at least one transmit element, and the transmit signal is in a radio frequency or visible range of the electromagnetic spectrum. A receive circuit is electrically connectable to the at least one receive element, where the receive circuit is configured to receive the response detected by the at least one receive element. A control system is connected to the transmit circuit and is configured to implement at least first and second frequency sweeps by the at least one transmit element. The first frequency sweep occurs over a first frequency range from a start frequency to an end frequency, the second frequency sweep occurs over a second frequency range from a start frequency to an end frequency, and the first frequency range and the second frequency range overlap one another. The first frequency range and the second frequency range where they overlap have first frequency steps and second frequency steps, respectively. The first frequency steps are the same as the second frequency steps, each of the frequency steps of the first frequency steps and the second frequency steps has an associated operation time, and the operation times of the first frequency steps are identical to the operation times of the second frequency steps.

In another embodiment described herein, a method of operating a sensor system is described. The sensor system includes a detector array having at least one transmit element and at least one receive element, where the at least one transmit element is positioned and arranged to transmit a transmit signal into a target, and the at least one receive element is positioned and arranged to detect a response resulting from transmission of the transmit signal by the at least one transmit element into the target. A transmit circuit is electrically connectable to the at least one transmit element where the transmit circuit is configured to generate the transmit signal to be transmitted by the at least one transmit element, and the transmit signal is in a radio frequency or visible range of the electromagnetic spectrum. In addition, a receive circuit is electrically connectable to the at least one receive element where the receive circuit is configured to receive a response detected by the at least one receive element. The method includes controlling the sensor system to implement at least a first frequency sweep and a second frequency sweep by the at least one transmit element, where the first frequency sweep occurs over a first frequency range from a start frequency to an end frequency, the second frequency sweep occurs over a second frequency range from a start frequency to an end frequency, and the first frequency range and the second frequency range overlap one another. The first frequency range and the second frequency range where they overlap have first frequency steps and second frequency steps, respectively. The first frequency steps are the same as the second frequency steps, each frequency step of the first frequency steps and the second frequency steps has an associated operation time, and the operation times of the first frequency steps are identical to the operation times of the second frequency steps.

DRAWINGS

FIG. 1 is a schematic depiction of an analyte sensor system with an analyte sensor relative to a target according to an embodiment.

FIGS. 2A-C illustrate different example orientations of antenna arrays that can be used in an embodiment of a sensor system described herein.

Like reference numbers represent like parts throughout.

DETAILED DESCRIPTION

Figure 6:
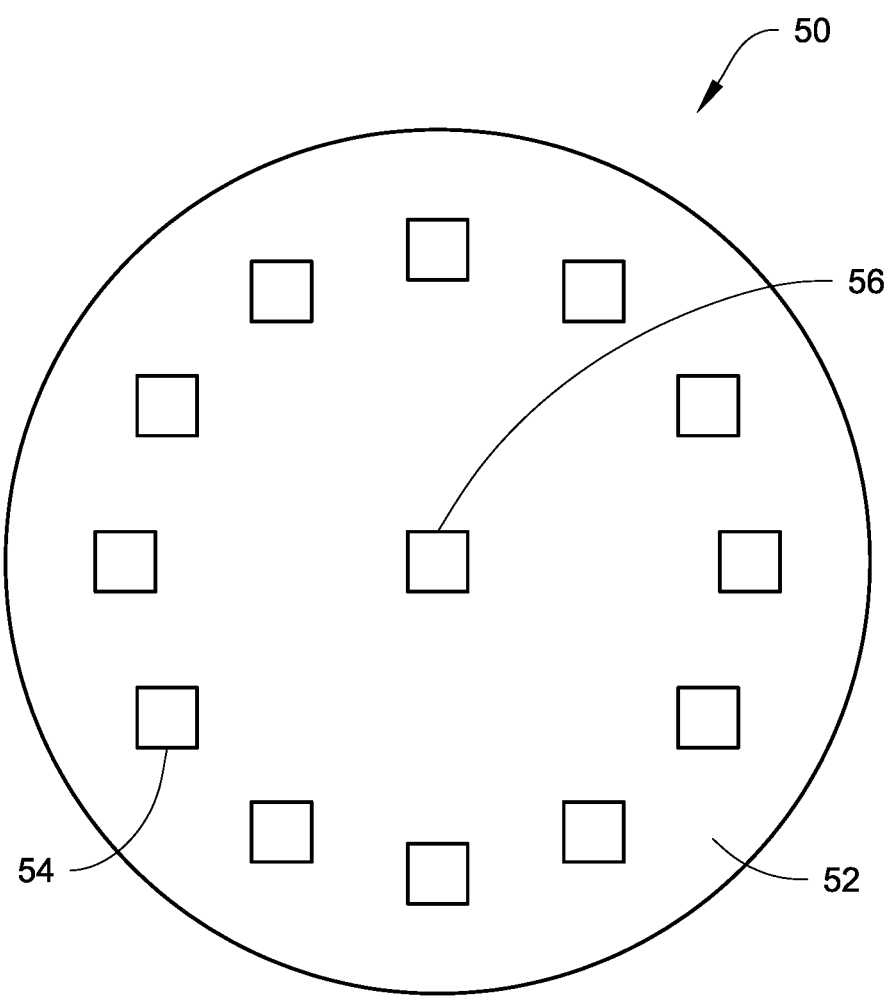
FIG. 6 is a schematic depiction of a portion of another embodiment of an analyte sensor system with an analyte sensor that uses electromagnetic energy in the form of light to perform analyte sensing described herein.
Figure 7:
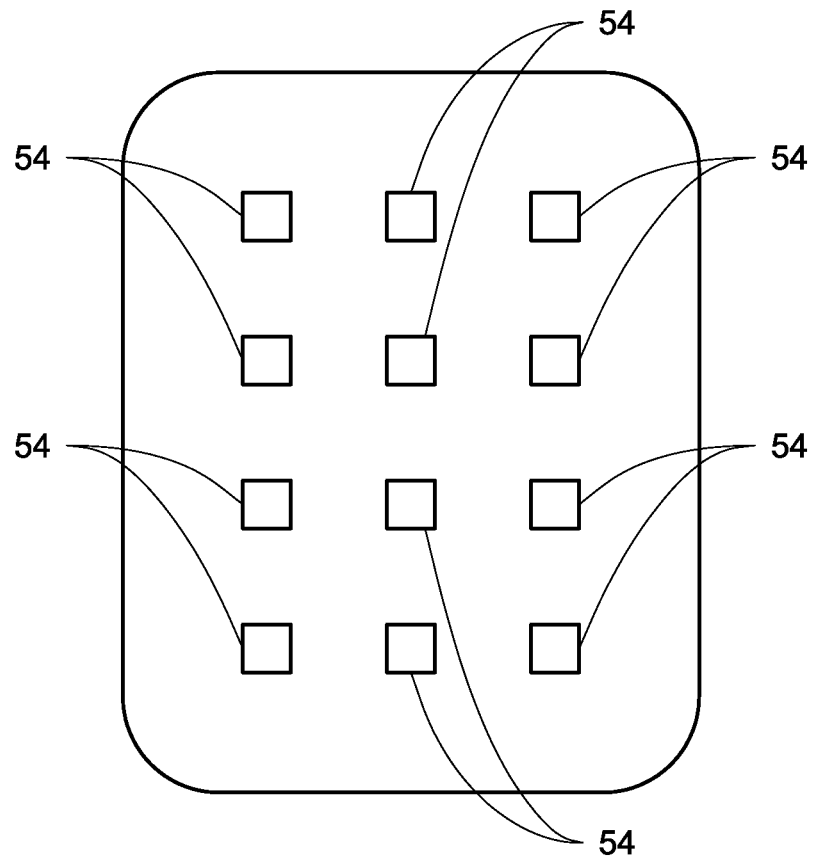
FIG. 7 illustrates another example of an analyte sensor system with an analyte sensor that uses electromagnetic energy in the form of light to perform analyte sensing described herein.

The following is a detailed description of apparatus, systems and methods of detecting an analyte via spectroscopic techniques using non-optical frequencies such as in the radio or microwave frequency bands of the electromagnetic spectrum or optical frequencies in the visible range of the electromagnetic spectrum. An analyte sensor described herein includes a detector array having at least one transmit element and at least one receive element. The transmit element and the receive element can be antennas (FIGS. 1-5) or light emitting elements such as light emitting diodes (FIGS. 6-7). In the following description, the transmit element and the receive element, whether they are antennas or light emitting diodes, may each be referred to as a detector element.

The following description together with FIGS. 1-5 will initially describe the analyte sensor system as including a detector array having two or more antennas. Later in the following description, together with FIGS. 6-7, the analyte sensor system is described as including a detector array that includes two or more light emitting devices such as light emitting diodes (LEDs). The detector array having two or more LEDs may also be described as an LED array.

In one embodiment, the sensor systems described herein can be used to detect the presence of at least one analyte in a target. In another embodiment, the sensor systems described herein can detect an amount or a concentration of the at least one analyte in the target. The target can be any target containing at least one analyte of interest that one may wish to detect. The target can be human or non-human, animal or non-animal, biological or non-biological. For example, the target can include, but is not limited to, human tissue, animal tissue, plant tissue, an inanimate object, soil, a fluid, genetic material, or a microbe. Non-limiting examples of targets include, but are not limited to, a fluid, for example blood, interstitial fluid, cerebral spinal fluid, lymph fluid or urine, human tissue, animal tissue, plant tissue, an inanimate object, soil, genetic material, or a microbe.

The detection by the sensors described herein can be non-invasive meaning that the sensor remains outside the target, such as the human body, and the detection of the analyte occurs without requiring removal of fluid or other removal from the target, such as the human body. In the of sensing in the human body, this non-invasive sensing may also be referred to as in vivo sensing. In other embodiments, the sensors described herein may be an in vitro sensor where the material containing the analyte has been removed, for example from a human body.

The analyte(s) can be any analyte that one may wish to detect. The analyte can be human or non-human, animal or non-animal, biological or non-biological. For example, the analyte(s) can include, but is not limited to, one or more of blood glucose, blood alcohol, white blood cells, or luteinizing hormone. The analyte(s) can include, but is not limited to, a chemical, a combination of chemicals, a virus, a bacteria, or the like. The analyte can be a chemical included in another medium, with non-limiting examples of such media including a fluid containing the at least one analyte, for example blood, interstitial fluid, cerebral spinal fluid, lymph fluid or urine, human tissue, animal tissue, plant tissue, an inanimate object, soil, genetic material, or a microbe. The analyte(s) may also be a non-human, non-biological particle such as a mineral or a contaminant.

The analyte(s) can include, for example, naturally occurring substances, artificial substances, metabolites, and/or reaction products. As non-limiting examples, the at least one analyte can include, but is not limited to, insulin, acarboxyprothrombin; acylcarnitine; adenine phosphoribosyl transferase; adenosine deaminase; albumin; alpha-fetoprotein; amino acid profiles (arginine (Krebs cycle), histidine/urocanic acid, homocysteine, phenylalanine/tyrosine, tryptophan); andrenostenedione; antipyrine; arabinitol enantiomers; arginase; benzoylecgonine (cocaine); biotinidase; biopterin; c-reactive protein; carnitine; pro-BNP; troponin; carnosinase; CD4; ceruloplasmin; chenodeoxycholic acid; chloroquine; cholesterol; cholinesterase; conjugated 1-β hydroxy-cholic acid; cortisol; creatine kinase; creatine kinase MM isoenzyme; cyclosporin A; d-penicillamine; de-ethylchloroquine; dehydroepiandrosterone sulfate; DNA (acetylator polymorphism, alcohol dehydrogenase, alpha 1-antitrypsin, cystic fibrosis, Duchenne/Becker muscular dystrophy, analyte-6-phosphate dehydrogenase, hemoglobin A, hemoglobin S, hemoglobin C, hemoglobin D, hemoglobin E, hemoglobin F, D-Punjab, beta-thalassemia, hepatitis B virus, HCMV, HIV-1, HTLV-1, Leber hereditary optic neuropathy, MCAD, RNA, PKU, Plasmodium vivax, sexual differentiation, 21-deoxycortisol); desbutylhalofantrine; dihydropteridine reductase; diptheria/tetanus antitoxin; erythrocyte arginase; erythrocyte protoporphyrin; esterase D; fatty acids/acylglycines; free β-human chorionic gonadotropin; free erythrocyte porphyrin; free thyroxine (FT4); free tri-iodothyronine (FT3); fumarylacetoacetase; galactose/gal-1-phosphate; galactose-1-phosphate uridyltransferase; gentamicin; analyte-6-phosphate dehydrogenase; glutathione; glutathione perioxidase; glycocholic acid; glycosylated hemoglobin; halofantrine; hemoglobin variants; hexosaminidase A; human erythrocyte carbonic anhydrase I;

17-alpha-hydroxyprogesterone; hypoxanthine phosphoribosyl transferase; immunoreactive trypsin; lactate; lead; lipoproteins ((a), B/A-1, β); lysozyme; mefloquine; netilmicin; phenobarbitone; phenytoin; phytanic/pristanic acid; progesterone; prolactin; prolidase; purine nucleoside phosphorylase; quinine; reverse tri-iodothyronine (rT3); selenium; serum pancreatic lipase; sissomicin; somatomedin C; specific antibodies (adenovirus, anti-nuclear antibody, anti-zeta antibody, arbovirus, Aujeszky's disease virus, dengue virus, *Dracunculus medinensis, Echinococcus granulosus, Entamoeba histolytica*, enterovirus, *Giardia duodenalisa, Helicobacter pylori*, hepatitis B virus, herpes virus, HIV-1, IgE (atopic disease), influenza virus, *Leishmania donovani*, leptospira, measles/mumps/rubella, *Mycobacterium leprae, Mycoplasma pneumoniae*, Myoglobin, *Onchocerca volvulus*, parainfluenza virus, *Plasmodium falciparum*, polio virus, *Pseudomonas aeruginosa*, respiratory syncytial virus, *rickettsia* (scrub typhus), *Schistosoma mansoni, Toxoplasma gondii, Trepenoma pallidium, Trypanosoma cruzi*/rangeli, vesicular *stomatis* virus, *Wuchereria bancrofti*, yellow fever virus); specific antigens (hepatitis B virus, HIV-1); succinylacetone; sulfadoxine; theophylline; thyrotropin (TSH); thyroxine (T4); thyroxine-binding globulin; trace elements; transferrin; UDP-galactose-4-epimerase; urea; uroporphyrinogen I synthase; vitamin A; white blood cells; and zinc protoporphyrin.

The analyte(s) can also include one or more chemicals introduced into the target. The analyte(s) can include a marker such as a contrast agent, a radioisotope, or other chemical agent. The analyte(s) can include a fluorocarbon-based synthetic blood. The analyte(s) can include a drug or pharmaceutical composition, with non-limiting examples including ethanol; *cannabis* (marijuana, tetrahydrocannabinol, hashish); inhalants (nitrous oxide, amyl nitrite, butyl nitrite, chlorohydrocarbons, hydrocarbons); cocaine (crack cocaine); stimulants (amphetamines, methamphetamines, Ritalin, Cylert, Preludin, Didrex, PreState, Voranil, Sandrex, Plegine); depressants (barbiturates, methaqualone, tranquilizers such as Valium, Librium, Miltown, Serax, Equanil, Tranxene); hallucinogens (phencyclidine, lysergic acid, mescaline, peyote, psilocybin); narcotics (heroin, codeine, morphine, opium, meperidine, Percocet, Percodan, Tussionex, Fentanyl, Darvon, Talwin, Lomotil); designer drugs (analogs of fentanyl, meperidine, amphetamines, methamphetamines, and phencyclidine, for example, Ecstasy); anabolic steroids; and nicotine. The analyte(s) can include other drugs or pharmaceutical compositions. The analyte(s) can include neurochemicals or other chemicals generated within the body, such as, for example, ascorbic acid, uric acid, dopamine, noradrenaline, 3-methoxytyramine (3MT), 3,4-Dihydroxyphenylacetic acid (DOPAC), Homovanillic acid (HVA), 5-Hydroxytryptamine (5HT), and 5-Hydroxyindoleacetic acid (FHIAA).

The sensor systems illustrated in FIGS. 1-5 and in FIGS. 6-7 operate by transmitting an electromagnetic signal (whether in the radio or microwave frequency range of the electromagnetic spectrum in FIGS. 1-5 or in the visible range of the electromagnetic spectrum in FIGS. 6-7) toward and into a target using a transmit element such as a transmit antenna or a transmit LED. A returning signal that results from the transmission of the transmitted signal is detected by a receive element such as a receive antenna or a photodetector. The signal(s) detected by the receive element can be analyzed to detect the analyte based on the intensity of the received signal(s) and reductions in intensity at one or more frequencies where the analyte absorbs the transmitted signal.

FIGS. 1-5 illustrate a non-invasive analyte sensor system that uses two or more antennas including a transmit antenna and a receive antenna. The transmit antenna and the receive antenna can be located near the target and operated as further described herein to assist in detecting at least one analyte in the target. The transmit antenna transmits a signal, which has at least two frequencies in the radio or microwave frequency range, toward and into the target. The signal with the at least two frequencies can be formed by separate signal portions, each having a discrete frequency, that are transmitted separately at separate times at each frequency. In another embodiment, the signal with the at least two frequencies may be part of a complex signal that includes a plurality of frequencies including the at least two frequencies. The complex signal can be generated by blending or multiplexing multiple signals together followed by transmitting the complex signal whereby the plurality of frequencies are transmitted at the same time. One possible technique for generating the complex signal includes, but is not limited to, using an inverse Fourier transformation technique. The receive antenna detects a response resulting from transmission of the signal by the transmit antenna into the target containing the at least one analyte of interest.

The transmit antenna and the receive antenna are decoupled (which may also be referred to as detuned or the like) from one another. Decoupling refers to intentionally fabricating the configuration and/or arrangement of the transmit antenna and the receive antenna to minimize direct communication between the transmit antenna and the receive antenna, preferably absent shielding. Shielding between the transmit antenna and the receive antenna can be utilized. However, the transmit antenna and the receive antenna are decoupled even without the presence of shielding.

An example of detecting an analyte using a non-invasive spectroscopy sensor operating in the radio or microwave frequency range of the electromagnetic spectrum is described in WO 2019/217461, the entire contents of which are incorporated herein by reference. The signal(s) detected by the receive antenna can be complex signals including a plurality of signal components, each signal component being at a different frequency. In an embodiment, the detected complex signals can be decomposed into the signal components at each of the different frequencies, for example through a Fourier transformation. In an embodiment, the complex signal detected by the receive antenna can be analyzed as a whole (i.e. without demultiplexing the complex signal) to detect the analyte as long as the detected signal provides enough information to make the analyte detection. In addition, the signal(s) detected by the receive antenna can be separate signal portions, each having a discrete frequency.

Figure 1:
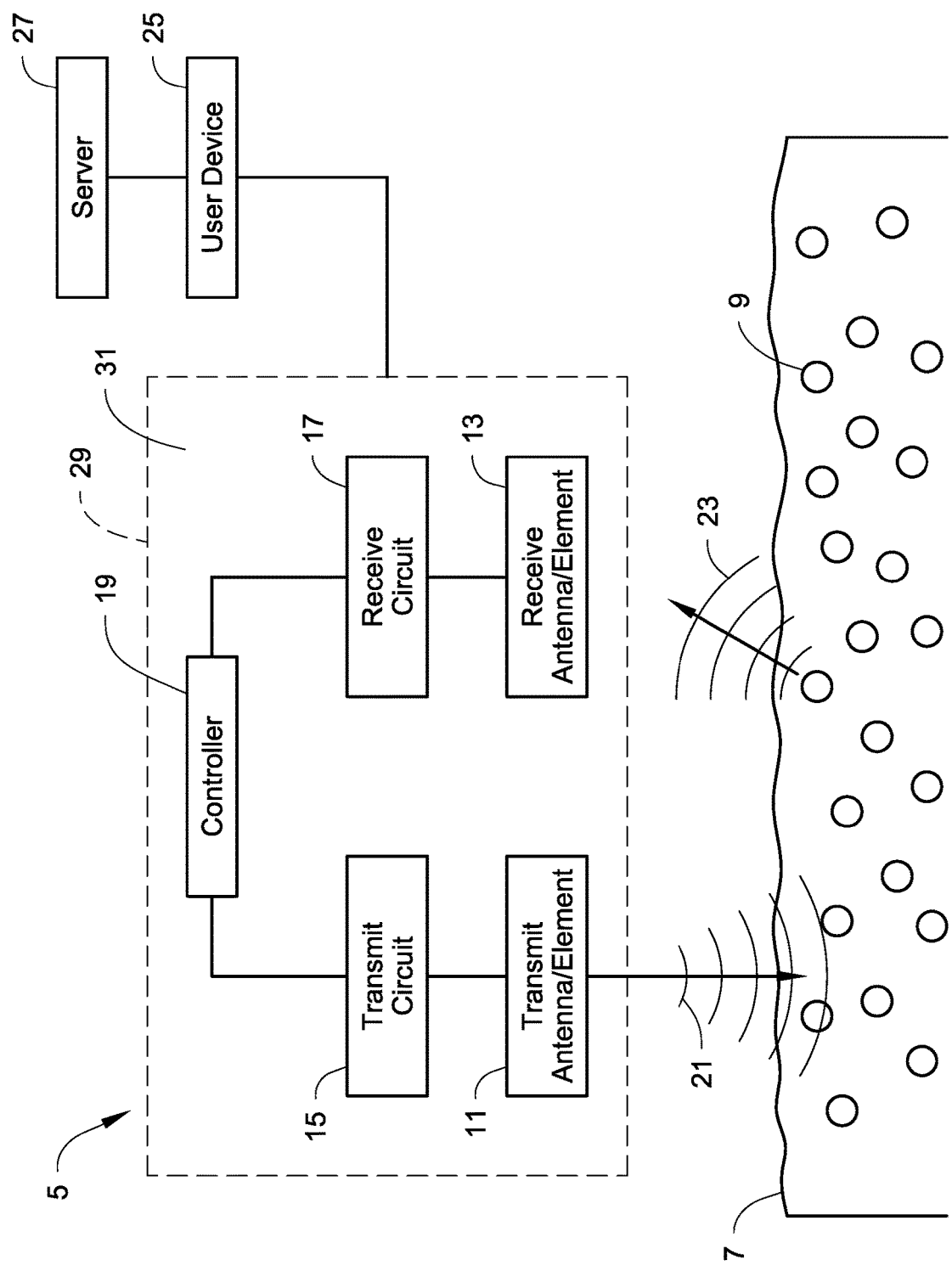

Referring now to FIG. 1, an embodiment of a non-invasive analyte sensor system with a non-invasive analyte sensor 5 is illustrated. The sensor 5 is depicted relative to a target 7 that contains an analyte of interest 9. In this example, the sensor 5 is depicted as including an antenna array that includes a transmit antenna/element 11 (hereinafter "transmit antenna 11") and a receive antenna/element 13 (hereinafter "receive antenna 13"). The sensor 5 further includes a transmit circuit 15, a receive circuit 17, and a controller 19. As discussed further below, the sensor 5 can also include a power supply, such as a battery (not shown in FIG. 1). In some embodiments, power can be provided from mains power, for example by plugging the sensor 5 into a wall socket via a cord connected to the sensor 5.

The transmit antenna 11 is positioned, arranged and configured to transmit a signal 21 that is in the radio frequency (RF) or microwave range of the electromagnetic spectrum into the target 7. The transmit antenna 11 can be an electrode or any other suitable transmitter of electromagnetic signals in the radio frequency (RF) or microwave range. The transmit antenna 11 can have any arrangement and orientation relative to the target 7 that is sufficient to allow the analyte sensing to take place. In one non-limiting embodiment, the transmit antenna 11 can be arranged to face in a direction that is substantially toward the target 7.

The signal 21 transmitted by the transmit antenna 11 is generated by the transmit circuit 15 which is electrically connectable to the transmit antenna 11. The transmit circuit 15 can have any configuration that is suitable to generate a transmit signal to be transmitted by the transmit antenna 11. Transmit circuits for generating transmit signals in the RF or microwave frequency range are well known in the art. In one embodiment, the transmit circuit 15 can include, for example, a connection to a power source, a frequency generator, and optionally filters, amplifiers or any other suitable elements for a circuit generating an RF or microwave frequency electromagnetic signal. In an embodiment, the signal generated by the transmit circuit 15 can have at least two discrete frequencies (i.e. a plurality of discrete frequencies), each of which is in the range from about 10 kHz to about 100 GHz. In another embodiment, each of the at least two discrete frequencies can be in a range from about 300 MHz to about 6000 MHz. In an embodiment, the transmit circuit 15 can be configured to sweep through a range of frequencies that are within the range of about 10 kHz to about 100 GHz, or in another embodiment a range of about 300 MHz to about 6000 MHz. In an embodiment, the transmit circuit 15 can be configured to produce a complex transmit signal, the complex signal including a plurality of signal components, each of the signal components having a different frequency. The complex signal can be generated by blending or multiplexing multiple signals together followed by transmitting the complex signal whereby the plurality of frequencies are transmitted at the same time.

The receive antenna 13 is positioned, arranged, and configured to detect one or more electromagnetic response signals 23 that result from the transmission of the transmit signal 21 by the transmit antenna 11 into the target 7 and impinging on the analyte 9. The receive antenna 13 can be an electrode or any other suitable receiver of electromagnetic signals in the radio frequency (RF) or microwave range. In an embodiment, the receive antenna 13 is configured to detect electromagnetic signals having at least two frequencies, each of which is in the range from about 10 kHz to about 100 GHz, or in another embodiment a range from about 300 MHz to about 6000 MHz. The receive antenna 13 can have any arrangement and orientation relative to the target 7 that is sufficient to allow detection of the response signal(s) 23 to allow the analyte sensing to take place. In one non-limiting embodiment, the receive antenna 13 can be arranged to face in a direction that is substantially toward the target 7.

The receive circuit 17 is electrically connectable to the receive antenna 13 and conveys the received response from the receive antenna 13 to the controller 19. The receive circuit 17 can have any configuration that is suitable for interfacing with the receive antenna 13 to convert the electromagnetic energy detected by the receive antenna 13 into one or more signals reflective of the response signal(s) 23. The construction of receive circuits are well known in the art. The receive circuit 17 can be configured to condition the signal(s) prior to providing the signal(s) to the controller 19, for example through amplifying the signal(s), filtering the signal(s), or the like. Accordingly, the receive circuit 17 may include filters, amplifiers, or any other suitable components for conditioning the signal(s) provided to the controller 19. In an embodiment, at least one of the receive circuit 17 or the controller 19 can be configured to decompose or demultiplex a complex signal, detected by the receive antenna 13, including a plurality of signal components each at different frequencies into each of the constituent signal components. In an embodiment, decomposing the complex signal can include applying a Fourier transform to the detected complex signal. However, decomposing or demultiplexing a received complex signal is optional. Instead, in an embodiment, the complex signal detected by the receive antenna can be analyzed as a whole (i.e. without demultiplexing the complex signal) to detect the analyte as long as the detected signal provides enough information to make the analyte detection.

The controller 19 controls the operation of the sensor 5. The controller 19, for example, can direct the transmit circuit 15 to generate a transmit signal to be transmitted by the transmit antenna 11. The controller 19 further receives signals from the receive circuit 17. The controller 19 can optionally process the signals from the receive circuit 17 to detect the analyte(s) 9 in the target 7. In one embodiment, the controller 19 may optionally be in communication with at least one external device 25 such as a user device and/or a remote server 27, for example through one or more wireless connections such as Bluetooth, wireless data connections such a 4G, 5G, LTE or the like, or Wi-Fi. If provided, the external device 25 and/or remote server 27 may process (or further process) the signals that the controller 19 receives from the receive circuit 17, for example to detect the analyte(s) 9. If provided, the external device 25 may be used to provide communication between the sensor 5 and the remote server 27, for example using a wired data connection or via a wireless data connection or Wi-Fi of the external device 25 to provide the connection to the remote server 27.

With continued reference to FIG. 1, the sensor 5 may include a sensor housing 29 (shown in dashed lines) that defines an interior space 31. Components of the sensor 5 may be attached to and/or disposed within the housing 29. For example, the transmit antenna 11 and the receive antenna 13 are attached to the housing 29. In some embodiments, the antennas 11, 13 may be entirely or partially within the interior space 31 of the housing 29. In some embodiments, the antennas 11, 13 may be attached to the housing 29 but at least partially or fully located outside the interior space 31. In some embodiments, the transmit circuit 15, the receive circuit 17 and the controller 19 are attached to the housing 29 and disposed entirely within the sensor housing 29.

The receive antenna 13 is decoupled or detuned with respect to the transmit antenna 11 such that electromagnetic coupling between the transmit antenna 11 and the receive antenna 13 is reduced. The decoupling of the transmit antenna 11 and the receive antenna 13 increases the portion of the signal(s) detected by the receive antenna 13 that is the response signal(s) 23 from the target 7, and minimizes direct receipt of the transmitted signal 21 by the receive antenna 13. The decoupling of the transmit antenna 11 and the receive antenna 13 results in transmission from the transmit antenna 11 to the receive antenna 13 having a reduced forward gain ($S_{21}$) and an increased reflection at output ($S_{22}$) compared to antenna systems having coupled transmit and receive antennas.

In an embodiment, coupling between the transmit antenna 11 and the receive antenna 13 is 95% or less. In another embodiment, coupling between the transmit antenna 11 and the receive antenna 13 is 90% or less. In another embodiment, coupling between the transmit antenna 11 and the receive antenna 13 is 85% or less. In another embodiment, coupling between the transmit antenna 11 and the receive antenna 13 is 75% or less.

Any technique for reducing coupling between the transmit antenna 11 and the receive antenna 13 can be used. For example, the decoupling between the transmit antenna 11 and the receive antenna 13 can be achieved by one or more intentionally fabricated configurations and/or arrangements between the transmit antenna 11 and the receive antenna 13 that is sufficient to decouple the transmit antenna 11 and the receive antenna 13 from one another.

For example, in one embodiment described further below, the decoupling of the transmit antenna 11 and the receive antenna 13 can be achieved by intentionally configuring the transmit antenna 11 and the receive antenna 13 to have different geometries from one another. Intentionally different geometries refers to different geometric configurations of the transmit and receive antennas 11, 13 that are intentional. Intentional differences in geometry are distinct from differences in geometry of transmit and receive antennas that may occur by accident or unintentionally, for example due to manufacturing errors or tolerances.

Another technique to achieve decoupling of the transmit antenna 11 and the receive antenna 13 is to provide appropriate spacing between each antenna 11, 13 that is sufficient to decouple the antennas 11, 13 and force a proportion of the electromagnetic lines of force of the transmitted signal 21 into the target 7 thereby minimizing or eliminating as much as possible direct receipt of electromagnetic energy by the receive antenna 13 directly from the transmit antenna 11 without traveling into the target 7. The appropriate spacing between each antenna 11, 13 can be determined based upon factors that include, but are not limited to, the output power of the signal from the transmit antenna 11, the size of the antennas 11, 13, the frequency or frequencies of the transmitted signal, and the presence of any shielding between the antennas. This technique helps to ensure that the response detected by the receive antenna 13 is measuring the analyte 9 and is not just the transmitted signal 21 flowing directly from the transmit antenna 11 to the receive antenna 13. In some embodiments, the appropriate spacing between the antennas 11, 13 can be used together with the intentional difference in geometries of the antennas 11, 13 to achieve decoupling.

In one embodiment, the transmit signal that is transmitted by the transmit antenna 11 can have at least two different frequencies, for example upwards of 7 to 12 different and discrete frequencies. In another embodiment, the transmit signal can be a series of discrete, separate signals with each separate signal having a single frequency or multiple different frequencies.

In one embodiment, the transmit signal (or each of the transmit signals) can be transmitted over a transmit time that is less than, equal to, or greater than about 300 ms. In another embodiment, the transmit time can be less than, equal to, or greater than about 200 ms. In still another embodiment, the transmit time can be less than, equal to, or greater than about 30 ms. The transmit time could also have a magnitude that is measured in seconds, for example 1 second, 5 seconds, 10 seconds, or more. In an embodiment, the same transmit signal can be transmitted multiple times, and then the transmit time can be averaged. In another embodiment, the transmit signal (or each of the transmit signals) can be transmitted with a duty cycle that is less than or equal to about 50%.

FIGS. 2A-2C illustrate examples of antenna arrays 33 that can be used in the sensor system 5 and how the antenna arrays 33 can be oriented. Many orientations of the antenna arrays 33 are possible, and any orientation can be used as long as the sensor 5 can perform its primary function of sensing the analyte 9.

In FIG. 2A, the antenna array 33 includes the transmit antenna 11 and the receive antenna 13 disposed on a substrate 35 which may be substantially planar. This example depicts the array 33 disposed substantially in an X-Y plane. In this example, dimensions of the antennas 11, 13 in the X and Y-axis directions can be considered lateral dimensions, while a dimension of the antennas 11, 13 in the Z-axis direction can be considered a thickness dimension. In this example, each of the antennas 11, 13 has at least one lateral dimension (measured in the X-axis direction and/or in the Y-axis direction) that is greater than the thickness dimension thereof (in the Z-axis direction). In other words, the transmit antenna 11 and the receive antenna 13 are each relatively flat or of relatively small thickness in the Z-axis direction compared to at least one other lateral dimension measured in the X-axis direction and/or in the Y-axis direction.

In use of the embodiment in FIG. 2A, the sensor and the array 33 may be positioned relative to the target 7 such that the target 7 is below the array 33 in the Z-axis direction or above the array 33 in the Z-axis direction whereby one of the faces of the antennas 11, 13 face toward the target 7. Alternatively, the target 7 can be positioned to the left or right sides of the array 33 in the X-axis direction whereby one of the ends of each one of the antennas 11, 13 face toward the target 7. Alternatively, the target 7 can be positioned to the sides of the array 33 in the Y-axis direction whereby one of the sides of each one of the antennas 11, 13 face toward the target 7.

The sensor 5 can also be provided with one or more additional antenna arrays in addition the antenna array 33. For example, FIG. 2A also depicts an optional second antenna array 33a that includes the transmit antenna 11 and the receive antenna 13 disposed on a substrate 35a which may be substantially planar. Like the array 33, the array 33a may also be disposed substantially in the X-Y plane, with the arrays 33, 33a spaced from one another in the X-axis direction.

In FIG. 2B, the antenna array 33 is depicted as being disposed substantially in the Y-Z plane. In this example, dimensions of the antennas 11, 13 in the Y and Z-axis directions can be considered lateral dimensions, while a dimension of the antennas 11, 13 in the X-axis direction can be considered a thickness dimension. In this example, each of the antennas 11, 13 has at least one lateral dimension (measured in the Y-axis direction and/or in the Z-axis direction) that is greater than the thickness dimension thereof (in the X-axis direction). In other words, the transmit antenna 11 and the receive antenna 13 are each relatively flat or of relatively small thickness in the X-axis direction compared to at least one other lateral dimension measured in the Y-axis direction and/or in the Z-axis direction.

In use of the embodiment in FIG. 2B, the sensor and the array 33 may be positioned relative to the target 7 such that the target 7 is below the array 33 in the Z-axis direction or above the array 33 in the Z-axis direction whereby one of the ends of each one of the antennas 11, 13 face toward the target 7. Alternatively, the target 7 can be positioned in front of or behind the array 33 in the X-axis direction whereby one of the faces of each one of the antennas 11, 13 face toward the target 7. Alternatively, the target 7 can be positioned to one of the sides of the array 33 in the Y-axis direction whereby one of the sides of each one of the antennas 11, 13 face toward the target 7.

In FIG. 2C, the antenna array 33 is depicted as being disposed substantially in the X-Z plane. In this example, dimensions of the antennas 11, 13 in the X and Z-axis directions can be considered lateral dimensions, while a dimension of the antennas 11, 13 in the Y-axis direction can be considered a thickness dimension. In this example, each of the antennas 11, 13 has at least one lateral dimension (measured in the X-axis direction and/or in the Z-axis direction) that is greater than the thickness dimension thereof (in the Y-axis direction). In other words, the transmit antenna 11 and the receive antenna 13 are each relatively flat or of relatively small thickness in the Y-axis direction compared to at least one other lateral dimension measured in the X-axis direction and/or in the Z-axis direction.

In use of the embodiment in FIG. 2C, the sensor and the array 33 may be positioned relative to the target 7 such that the target 7 is below the array 33 in the Z-axis direction or above the array 33 in the Z-axis direction whereby one of the ends of each one of the antennas 11, 13 face toward the target 7. Alternatively, the target 7 can be positioned to the left or right sides of the array 33 in the X-axis direction whereby one of the sides of each one of the antennas 11, 13 face toward the target 7. Alternatively, the target 7 can be positioned in front of or in back of the array 33 in the Y-axis direction whereby one of the faces of each one of the antennas 11, 13 face toward the target 7.

The arrays 33, 33a in FIGS. 2A-2C need not be oriented entirely within a plane such as the X-Y plane, the Y-Z plane or the X-Z plane. Instead, the arrays 33, 33a can be disposed at angles to the X-Y plane, the Y-Z plane and the X-Z plane.

Decoupling Antennas Using Differences in Antenna Geometries

As mentioned above, one technique for decoupling the transmit antenna 11 from the receive antenna 13 is to intentionally configure the transmit antenna 11 and the receive antenna 13 to have intentionally different geometries. Intentionally different geometries refers to differences in geometric configurations of the transmit and receive antennas 11, 13 that are intentional, and is distinct from differences in geometry of the transmit and receive antennas 11, 13 that may occur by accident or unintentionally, for example due to manufacturing errors or tolerances when fabricating the antennas 11, 13.

The different geometries of the antennas 11, 13 may manifest itself, and may be described, in a number of different ways. For example, in a plan view of each of the antennas 11, 13 (such as in FIGS. 3A-C), the shapes of the perimeter edges of the antennas 11, 13 may be different from one another. The different geometries may result in the antennas 11, 13 having different surface areas in plan view. The different geometries may result in the antennas 11, 13 having different aspect ratios in plan view (i.e. a ratio of their sizes in different dimensions; for example, as discussed in further detail below, the ratio of the length divided by the width of the antenna 11 may be different than the ratio of the length divided by the width for the antenna 13). In some embodiments, the different geometries may result in the antennas 11, 13 having any combination of different perimeter edge shapes in plan view, different surface areas in plan view, and/or different aspect ratios. In some embodiments, the antennas 11, 13 may have one or more holes formed therein (see FIG. 2B) within the perimeter edge boundary, or one or more notches formed in the perimeter edge (see FIG. 2B).

So as used herein, a difference in geometry or a difference in geometrical shape of the antennas 11, 13 refers to any intentional difference in the figure, length, width, size, shape, area closed by a boundary (i.e. the perimeter edge), etc. when the respective antenna 11, 13 is viewed in a plan view.

The antennas 11, 13 can have any configuration and can be formed from any suitable material that allows them to perform the functions of the antennas 11, 13 as described herein. In one embodiment, the antennas 11, 13 can be formed by strips of material. A strip of material can include a configuration where the strip has at least one lateral dimension thereof greater than a thickness dimension thereof when the antenna is viewed in a plan view (in other words, the strip is relatively flat or of relatively small thickness compared to at least one other lateral dimension, such as length or width when the antenna is viewed in a plan view as in FIGS. 3A-C). A strip of material can include a wire. The antennas 11, 13 can be formed from any suitable conductive material(s) including metals and conductive non-metallic materials. Examples of metals that can be used include, but are not limited to, copper or gold. Another example of a material that can be used is non-metallic materials that are doped with metallic material to make the non-metallic material conductive.

Figure 3A:
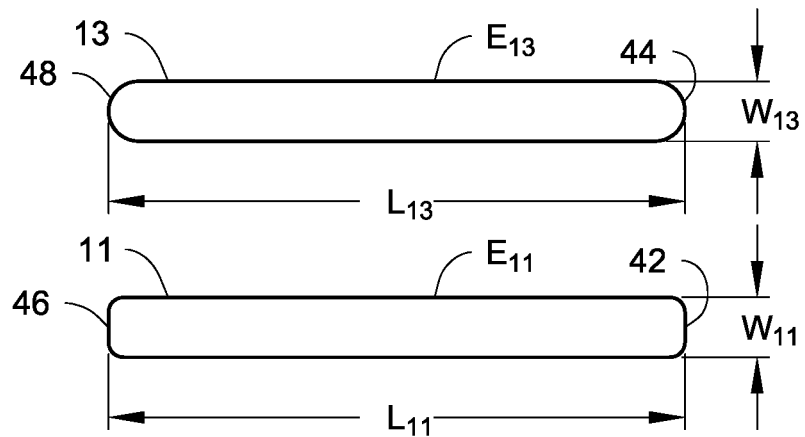
FIGS. 3A-3C illustrate different examples of transmit and receive antennas with different geometries.
Figure 3B:
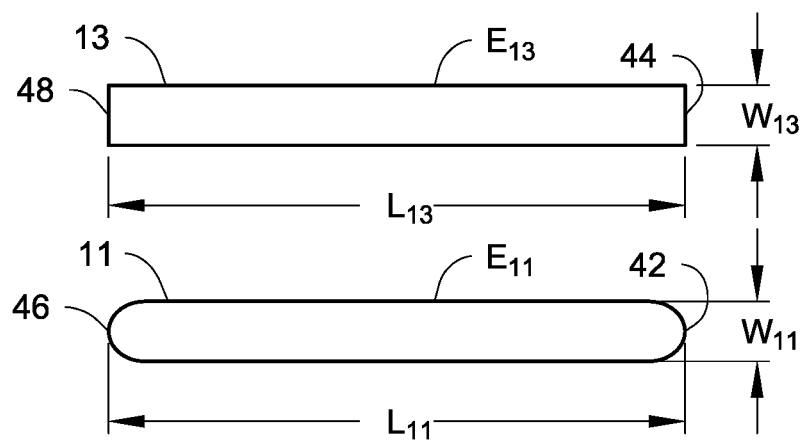
Figure 3C:
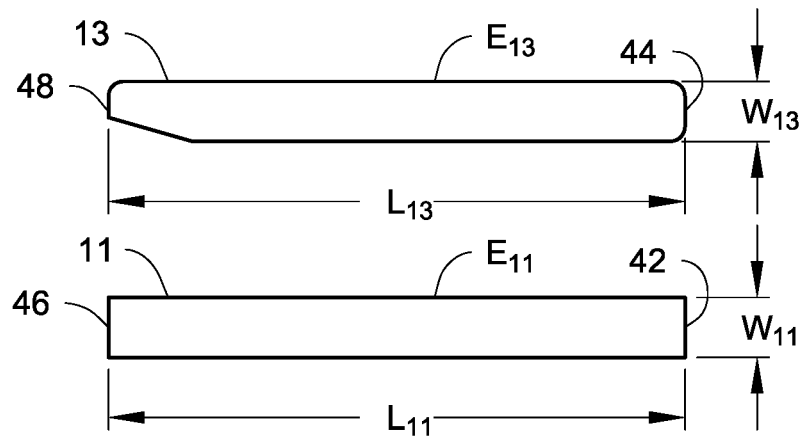

In FIGS. 2A-2C, the antennas 11, 13 within each one of the arrays 33, 33a have different geometries from one another. In addition, FIGS. 3A-C illustrate plan views of additional examples of the antennas 11, 13 having different geometries from one another. The examples in FIGS. 2A-2C and 3A-C are not exhaustive and many different configurations are possible.

FIG. 3A illustrates a plan view of an antenna array having two antennas with different geometries. In this example, the antennas 11, 13 are illustrated as substantially linear strips each with a lateral length $L_{11}$, $L_{13}$, a lateral width $W_{11}$, $W_{13}$, and a perimeter edge $E_{11}$, $E_{13}$. The perimeter edges $E_{11}$, $E_{13}$ extend around the entire periphery of the antennas 11, 13 and bound an area in plan view. In this example, the lateral length $L_{11}$, $L_{13}$ and/or the lateral width $W_{11}$, $W_{13}$ is greater than a thickness dimension of the antennas 11, 13 extending into/from the page when viewing FIG. 3A. In this example, the antennas 11, 13 differ in geometry from one another in that the shapes of the ends of the antennas 11, 13 differ from one another. For example, when viewing FIG. 3A, the right end 42 of the antenna 11 has a different shape than the right end 44 of the antenna 13. Similarly, the left end 46 of the antenna 11 may have a similar shape as the right end 42, but differs from the left end 48 of the antenna 13 which may have a similar shape as the right end 44. It is also possible that the lateral lengths $L_{11}$, $L_{13}$ and/or the lateral widths $W_{11}$, $W_{13}$ of the antennas 11, 13 could differ from one another.

FIG. 3B illustrates another plan view of an antenna array having two antennas with different geometries that is somewhat similar to FIG. 3A. In this example, the antennas 11, 13 are illustrated as substantially linear strips each with the lateral length $L_{11}$, $L_{13}$, the lateral width $W_{11}$, $W_{13}$, and the perimeter edge $E_{11}$, $E_{13}$. The perimeter edges $E_{11}$, $E_{13}$ extend around the entire periphery of the antennas 11, 13 and bound an area in plan view. In this example, the lateral length $L_{11}$, $L_{13}$ and/or the lateral width $W_{11}$, $W_{13}$ is greater than a thickness dimension of the antennas 11, 13 extending into/from the page when viewing FIG. 3B. In this example, the antennas 11, 13 differ in geometry from one another in that the shapes of the ends of the antennas 11, 13 differ from one another. For example, when viewing FIG. 3B, the right end 42 of the antenna 11 has a different shape than the right end 44 of the antenna 13. Similarly, the left end 46 of the antenna 11 may have a similar shape as the right end 42, but differs from the left end 48 of the antenna 13 which may have a similar shape as the right end 44. In addition, the lateral widths $W_{11}$, $W_{13}$ of the antennas 11, 13 differ from one another. It is also possible that the lateral lengths $L_{11}$, $L_{13}$ of the antennas 11, 13 could differ from one another.

FIG. 3C illustrates another plan view of an antenna array having two antennas with different geometries that is somewhat similar to FIGS. 3A and 3B. In this example, the antennas 11, 13 are illustrated as substantially linear strips each with the lateral length $L_{11}$, $L_{13}$, the lateral width $W_{11}$, $W_{13}$, and the perimeter edge $E_{11}$, $E_{13}$. The perimeter edges $E_{11}$, $E_{13}$ extend around the entire periphery of the antennas 11, 13 and bound an area in plan view. In this example, the lateral length $L_{11}$, $L_{13}$ and/or the lateral width $W_{11}$, $W_{13}$ is greater than a thickness dimension of the antennas 11, 13 extending into/from the page when viewing FIG. 3C. In this example, the antennas 11, 13 differ in geometry from one another in that the shapes of the ends of the antennas 11, 13 differ from one another. For example, when viewing FIG. 3C, the right end 42 of the antenna 11 has a different shape than the right end 44 of the antenna 13. Similarly, the left end 46 of the antenna 11 may have a similar shape as the right end 42, but differs from the left end 48 of the antenna 13 which may have a similar shape as the right end 44. In addition, the lateral widths $W_{11}$, $W_{13}$ of the antennas 11, 13 differ from one another. It is also possible that the lateral lengths $L_{11}$, $L_{13}$ of the antennas 11, 13 could differ from one another.

Figure 4A:
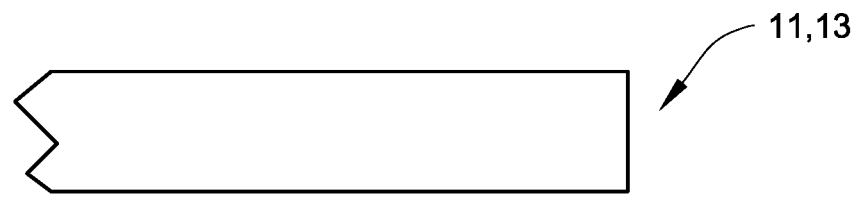
FIGS. 4A, 4B, 4C and 4D illustrate additional examples of different shapes that the ends of the transmit and receive antennas can have.
Figure 4B:
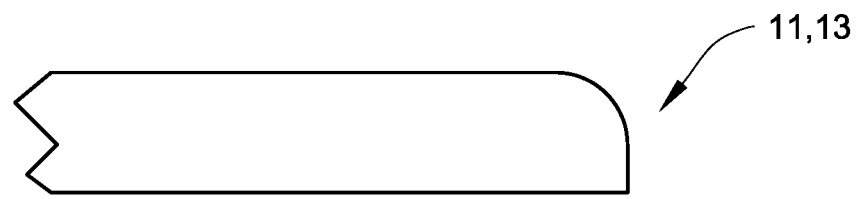
Figure 4C:
Figure 4D:
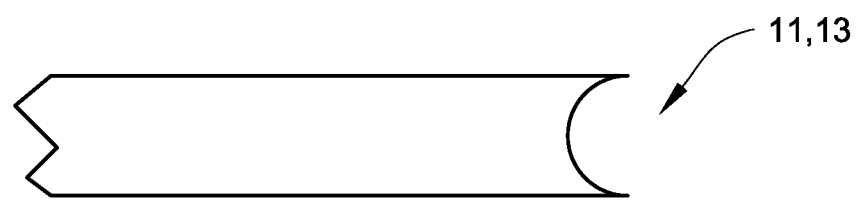

FIGS. 4A-D are plan views of additional examples of different shapes that the ends of the transmit and receive antennas 11, 13 can have to achieve differences in geometry. Either one of, or both of, the ends of the antennas 11, 13 can have the shapes in FIGS. 4A-D, including in the embodiments in FIGS. 3A-C. FIG. 4A depicts the end as being generally rectangular. FIG. 4B depicts the end as having one rounded corner while the other corner remains a right angle. FIG. 4C depicts the entire end as being rounded or outwardly convex. FIG. 4D depicts the end as being inwardly concave. Many other shapes are possible.

Figure 5:
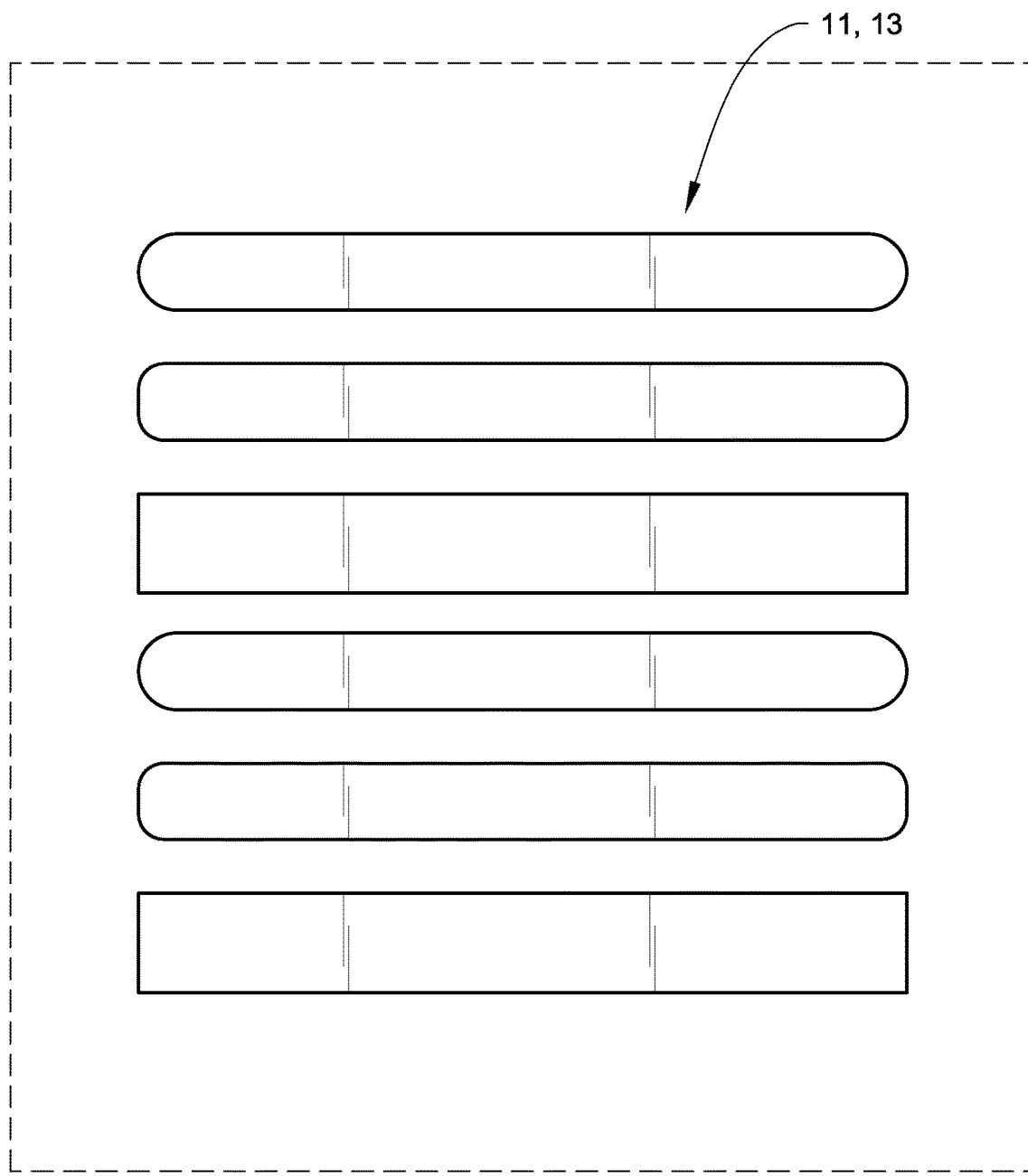
FIG. 5 illustrates another example of an antenna array that can be used.

FIG. 5 illustrates another plan view of an antenna array having six antennas illustrated as substantially linear strips. In this example, the antennas differ in geometry from one another in that the shapes of the ends of the antennas, the lateral lengths and/or the lateral widths of the antennas differ from one another.

Another technique to achieve decoupling of the antennas is to use an appropriate spacing between each antenna with the spacing being sufficient to force most or all of the signal(s) transmitted by the transmit antenna into the target, thereby minimizing the direct receipt of electromagnetic energy by the receive antenna directly from the transmit antenna. The appropriate spacing can be used by itself to achieve decoupling of the antennas. In another embodiment, the appropriate spacing can be used together with differences in geometry of the antennas to achieve decoupling.

Referring to FIG. 2A, there is a spacing D between the transmit antenna 11 and the receive antenna 13 at the location indicated. The spacing D between the antennas 11, 13 may be constant over the entire length (for example in the X-axis direction) of each antenna 11, 13, or the spacing D between the antennas 11, 13 could vary. Any spacing D can be used as long as the spacing D is sufficient to result in most or all of the signal(s) transmitted by the transmit antenna 11 reaching the target and minimizing the direct receipt of electromagnetic energy by the receive antenna 13 directly from the transmit antenna 11, thereby decoupling the antennas 11, 13 from one another.

In addition, there is preferably a maximum spacing and a minimum spacing between the transmit antenna 11 and the receive antenna 13. The maximum spacing may be dictated by the maximum size of the housing 29. In one embodiment, the maximum spacing can be about 50 mm. In one embodiment, the minimum spacing can be from about 1.0 mm to about 5.0 mm.

FIG. 6 schematically depicts another example of a non-invasive analyte sensor 50 that forms a portion of another embodiment of a non-invasive analyte sensor system. The non-invasive analyte sensor 50 uses electromagnetic energy in the form of light waves at selected electromagnetic frequencies to perform non-invasive analyte sensing described herein. The sensor 50 includes a housing 52 and a sensor array that includes a plurality of transmit elements 54 each of which can emit electromagnetic energy in the form of light. In this example, the transmit elements 54 are disposed in an array surrounding a receive element 56 which can be a photodetector. The illustrated example depicts the array as having a total of twelve of the elements 54 arranged in a circular array around the receive element 56. However, a larger or smaller number of the elements 54 can be provided in the array. In addition, the array can have an arrangement other than being a circular array. The separate receive element 56 is not necessary if one of the elements 54 is controlled to function as a receive element as described in detail below with respect to LEDs that can function to both emit light and detect light.

FIG. 7 illustrates another embodiment similar to FIG. 6. In FIG. 7, each of the elements 54 are controlled in a manner whereby any one or more of the elements 54 can emit light (and thereby function as a transmit element) and any one or more of the elements 54 can act as a light detector (and thereby function as a receive element). In FIG. 7, since an element 54 can function as a transmit element or as a receive element, the use of a separate receive element 56 as in FIG. 6 is not required. However, the separate receive element 56 can be included if desired. The illustrated example depicts the array as having a total of twelve of the elements 54 arranged into a 3×4 or 4×3 array. However, a larger or smaller number of the elements 54 can be provided in the array. In addition, the array can have other arrangements including the elements 54 being disposed in a circular array.

In one embodiment, the elements 54 in FIGS. 6 and 7 may be light emitting diodes (LEDs) and the array that includes the LEDs can be referred to as an LED array. LEDs that can be selectively controlled to emit light (i.e. a photoemitter) or detect light (i.e. a photodetector) are known. See Stojanovic et al., An optical sensing approach based on light emitting diodes, Journal of Physics: Conference Series 76 (2007); Rossiter et al., A novel tactile sensor using a matrix of LEDs operating in both photoemitter and photodetector modes, Proc of 4th IEEE International Conference on Sensors (IEEE Sensors 2005). See also U.S. Pat. No. 4,202,000 the entire contents of which are incorporated herein by reference.

Figure 8:
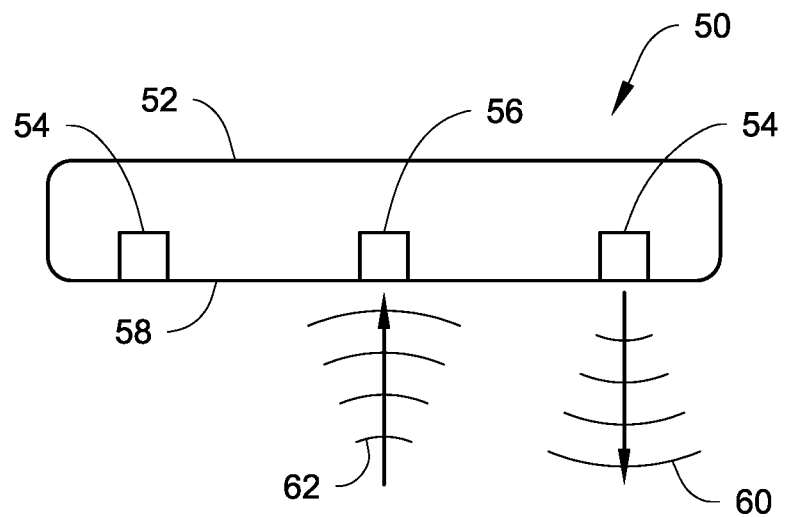
FIG. 8 depicts an example operation of the sensor system of FIG. 6.

Referring to FIG. 8, in the embodiments of FIGS. 6 and 7 some or all the elements 54 may be flush with a surface 58 of the housing 52 so that light emitted by each transmit element 54 may be transmitted from the sensor 50 and receive element 56 (or one of the elements 54 acting as a receive element) detects returning light. In another embodiment, some or all of the transmit elements 54 may be recessed within the housing 52 but the light from each transit element 54 is suitably channeled to the outside and returning light suitably channeled to the receive elements 54. In still another embodiment, some or all of the transmit elements 54 may project (partially or completely) from the surface 58 of the housing 52.

In FIGS. 6 and 7, when the elements 54 are LEDs, the LEDs can be controlled in a manner whereby any one or more of the LEDs can emit light. In addition, the receive element 56 of FIG. 6 can act as a light detector, or any one or more of the LEDs in FIGS. 6 and 7 can be controlled to act as a light detector. The LEDs that are used preferably permit at least two different wavelengths of light to be emitted. In another embodiment, at least three or more different wavelengths of light can be emitted. In one embodiment, each one of the LEDs can emit a different wavelength of light. In one embodiment, two or more of the LEDs can emit the same wavelength of light. The LED's can emit wavelengths that are in the human visible spectrum (for example, about 380 to about 760 nm) including, but not limited to, wavelengths that are visibly perceived as blue light, red light, green light, white light, orange light, yellow light, and other colors, as well as emit wavelengths that are not in the human visible spectrum including, but not limited to, infrared wavelengths. Combinations of wavelengths in the visible and non-visible spectrums may also be used. The light waves emitted by the sensor 50 function in a manner similar to the RF waves emitted by the sensor 5 in FIGS. 1-5 since both are electromagnetic waves. For example, referring to FIG. 8, light waves 60 emitted by the element 54 penetrate into a target and reflect from an analyte in the target to form the returning light waves 62 which are detected, for example the receive element 56 (or by an LED acting as a receive element).

Figure 9:
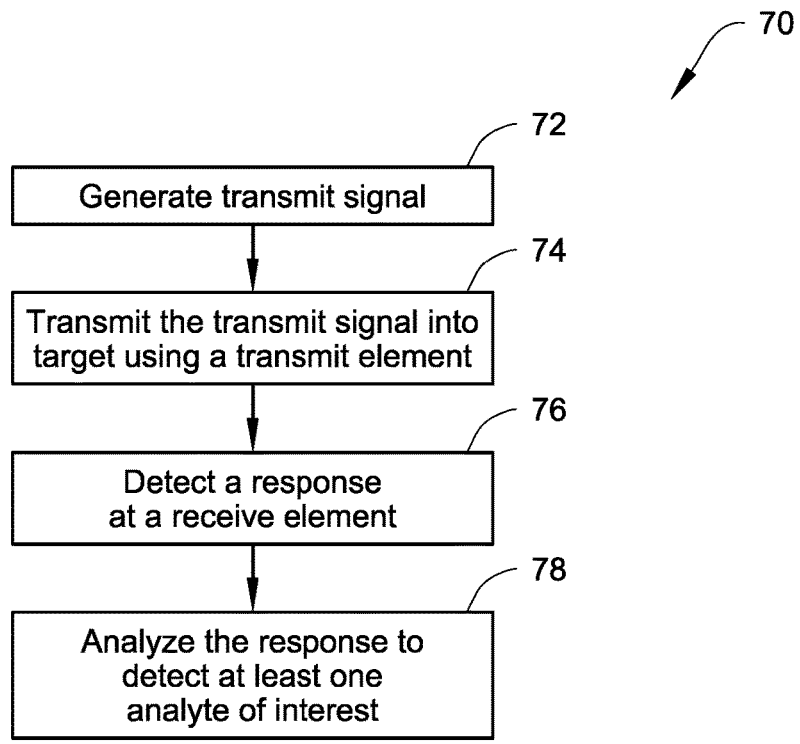
FIG. 9 is a flowchart of a method for detecting an analyte according to an embodiment.

With reference now to FIG. 9, one embodiment of a method 70 for detecting at least one analyte in a target is depicted. The method in FIG. 9 can be practiced using any of the embodiments of sensor devices described herein including the sensor 5 and the sensor 50. In order to detect the analyte, the sensor 5, 50 is placed in relatively close proximity to the target. Relatively close proximity means that the sensor 5, 50 can be close to but not in direct physical contact with the target, or alternatively the sensor 5, 50 can be placed in direct, intimate physical contact with the target. The spacing between the sensor 5, 50 and the target can be dependent upon a number of factors, such as the power of the transmitted signal. Assuming the sensor 5, 50 is properly positioned relative to the target, at box 72 the transmit signal is generated, for example by the transmit circuit 15. The transmit signal is then provided to the transmit element (11 or 54) which, at box 74, transmits the transmit signal toward and into the target. At box 76, a response resulting from the transmit signal contacting the analyte(s) is then detected by the receive element (13, 54, or 56). The receive circuit obtains the detected response from the receive element and provides the detected response to the controller. At box 78, the detected response can then be analyzed to detect at least one analyte. The analysis can be performed by the controller 19 and/or by the external device 25 and/or by the remote server 27.

Figure 10:
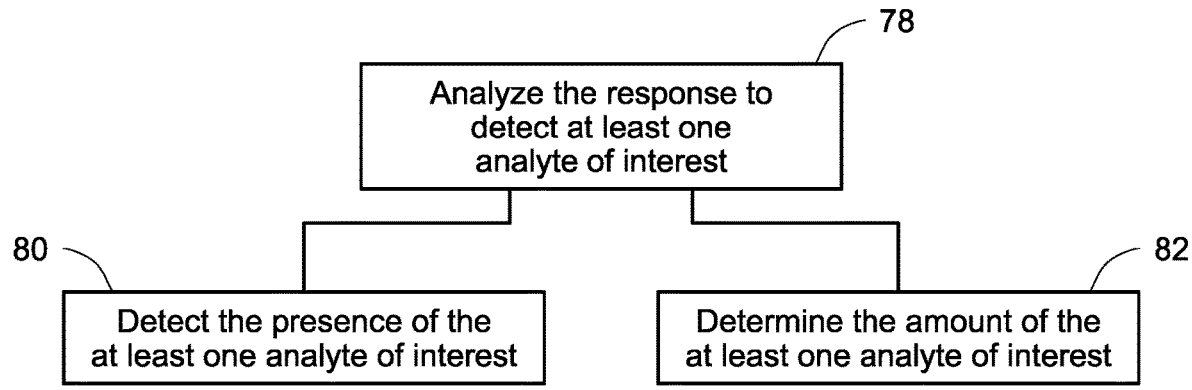
FIG. 10 is a flowchart of analysis of a response according to an embodiment.

Referring to FIG. 10, the analysis at box 78 in the method 70 can take a number of forms. In one embodiment, at box 80, the analysis can simply detect the presence of the analyte, i.e. is the analyte present in the target. Alternatively, at box 82, the analysis can determine the amount of the analyte that is present.

For example, in the case of the sensor being the sensor 5 and the signal being in the radio frequency range, the interaction between the transmitted signal and the analyte may, in some cases, increase the intensity of the signal(s) that is detected by the receive antenna, and may, in other cases, decrease the intensity of the signal(s) that is detected by the receive antenna. For example, in one non-limiting embodiment, when analyzing the detected response, compounds in the target, including the analyte of interest that is being detected, can absorb some of the transmit signal, with the absorption varying based on the frequency of the transmit signal. The response signal detected by the receive antenna may include drops in intensity at frequencies where compounds in the target, such as the analyte, absorb the transmit signal. The frequencies of absorption are particular to different analytes. The response signal(s) detected by the receive antenna can be analyzed at frequencies that are associated with the analyte of interest to detect the analyte based on drops in the signal intensity corresponding to absorption by the analyte based on whether such drops in signal intensity are observed at frequencies that correspond to the absorption by the analyte of interest. A similar technique can be employed with respect to increases in the intensity of the signal(s) caused by the analyte.

Detection of the presence of the analyte can be achieved, for example, by identifying a change in the signal intensity detected by the receive antenna at a known frequency associated with the analyte. The change may be a decrease in the signal intensity or an increase in the signal intensity depending upon how the transmit signal interacts with the analyte. The known frequency associated with the analyte can be established, for example, through testing of solutions known to contain the analyte. Determination of the amount of the analyte can be achieved, for example, by identifying a magnitude of the change in the signal at the known frequency, for example using a function where the input variable is the magnitude of the change in signal and the output variable is an amount of the analyte. The determination of the amount of the analyte can further be used to determine a concentration, for example based on a known mass or volume of the target. In an embodiment, presence of the analyte and determination of the amount of analyte may both be determined, for example by first identifying the change in the detected signal to detect the presence of the analyte, and then processing the detected signal(s) to identify the magnitude of the change to determine the amount.

In operation of either one of the sensors 5, 50 of FIGS. 1-8, one or more frequency sweeps or scan routines can implemented. The frequency sweeps can be implemented at a number of discrete frequencies (r frequency targets) over a range of frequencies. An example of a frequency sweep in a non-invasive analyte sensor using frequencies in the radio/microwave frequency range is described in WO 2019/217461, the entire contents of which are incorporated herein by reference. In the case of the sensor 50, a frequency sweep can be implemented with the sensor 50 at a number of discrete electromagnetic frequencies in the visible wavelength range over a range of electromagnetic frequencies based on the different wavelengths of the LEDs. A response spectra is detected by the receive element 56 or by the element 54 functioning as a photodetector with the response spectra being correlated to a particular analyte and analyte concentration.

Figure 11:
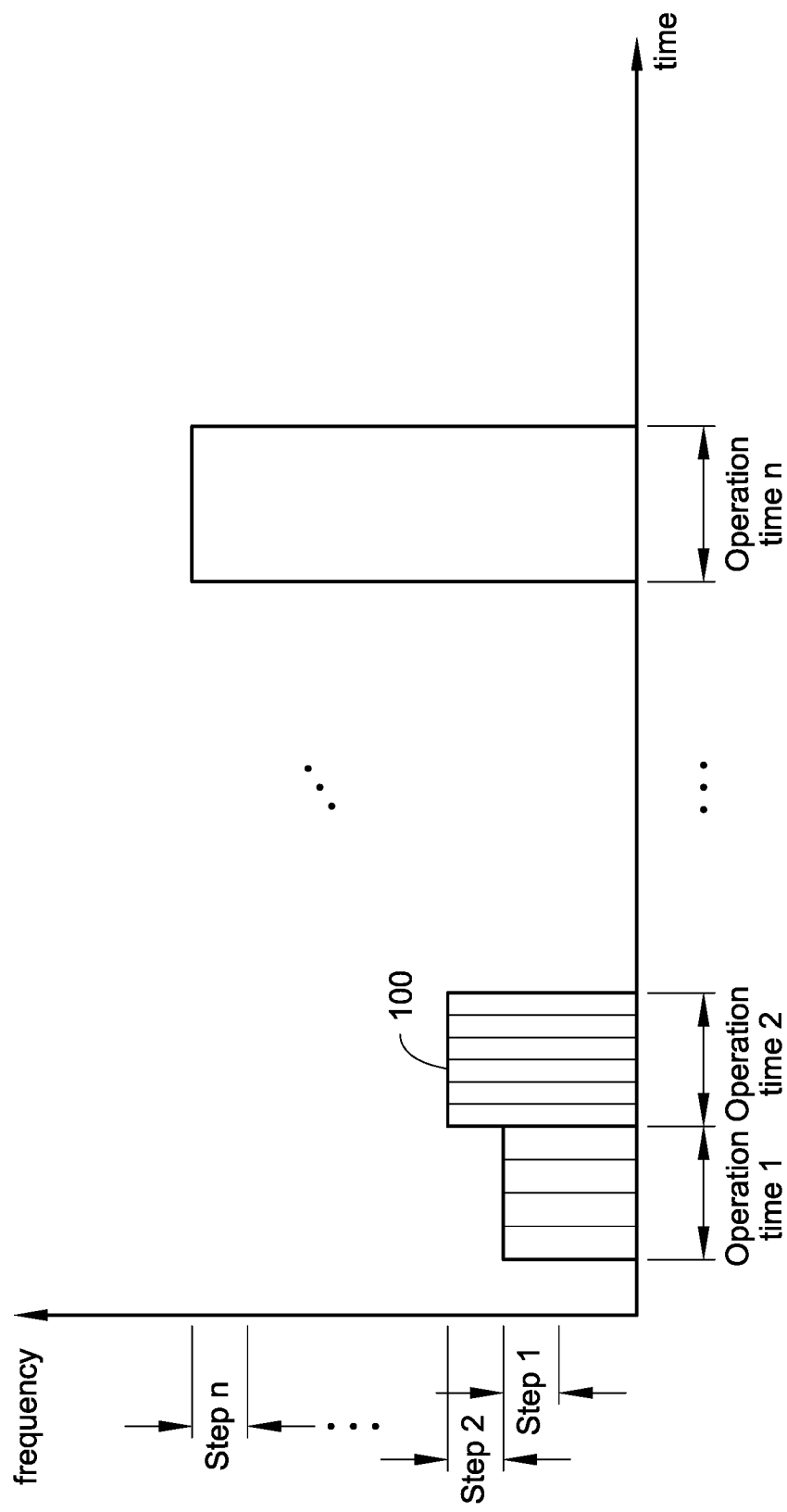
FIG. 11 depicts an example of a frequency sweep.

An example of a frequency sweep is illustrated in FIG. 11 where frequency is plotted against time. The sweep occurs over a frequency range from a start frequency to an end frequency. In one embodiment, in the case of the radio frequency sensor 5, the start frequency can be about 10 kHz and the end frequency can be about 100 GHz. However, the start frequency of the frequency sweep can be about 100 GHz and the end frequency can be about 10 kHz. In the case of the sensor 50, the start frequency can be about 400 THz (i.e. about 380 nm) and the end frequency can be about 790 THz (i.e. about 760 nm). However, the start frequency of the frequency sweep can be about 790 THz and the end frequency can be about 400 THz.

At selected target frequencies within the frequency range, the transmit element emits at least one transmit signal at the associated target frequency. The sweep includes a plurality of frequency steps 1, 2 . . . n each of which defines an incremental change (increase or decrease) in frequency from one target frequency to the next target frequency. The frequency steps in the frequency sweep can be the same as one another or some of the frequency steps can be different from one another. For example, in one embodiment, each frequency step can be 1 Hz or 1 kHz or 1 THz, 5 Hz or 5 kHz or 5 THz, 10 Hz or 10 kHz or 10 THz, etc. At the conclusion of emitting a signal at a particular target frequency, the controller initiates a step change to the next target frequency by increasing or decreasing the frequency by the frequency step to transmit one or more signals at the next target frequency.

Each frequency step has an associated operation time. The operation time is the total time (processor clock time) from the completion of operation at one target frequency to the completion of operation at the next target frequency (i.e. the end of the processor clock at the one target frequency to the end of the processor clock at the next target frequency), or from the start of operation at one target frequency to the start of operation at the next target frequency. Each operation time is made-up of a plurality of sub-operations 100 and associated sub-operation times which are operational delays within and that make up the block of operation time. Sub-operations 100 include all the operational delays that occur in transitioning from one target frequency to the next target frequency and generating and transmitting the signal at the next target frequency. For example, examples of sub-operation time delays can include, but are not limited to: the time to write data to a memory chip; the time to read data/instructions from memory or the processor; the time to step from a completed target frequency to the next target frequency; the time to generate a signal to be transmitted at the next target frequency; the time to transmit the signal from the signal generator to the transmit element; the time to transmit one or more of the signals by the transmit element at the next target frequency; etc. The number and times of the sub-operation time delays in each block of operation time can vary.

In one embodiment, the frequency sweep can be controlled by the controller so that all of the blocks of operation times across the entire sweep are the same as one another. For example, in one embodiment, each block of operation time over the entire frequency sweep can be 30 µs. In another embodiment, the frequency sweep can be controlled so that at least some of the blocks of operation times across the entire frequency sweep differ from one another. For example, in one embodiment, one or more of the operation times can be 30 µs, one or more of the operation times can be 25 µs, one or more of the operation times can be 35 µs, one or more of the operation times can be 100 ms, etc. When controlling the frequency sweeps, the controller can introduce delay into one or more operation times to achieve the desired operation time. For example, in one of the sub-operations 100 at a particular target frequency, the signal at that particular target frequency may be transmitted multiple times instead of transmitted a single time. In another embodiment, the controller can accelerate or eliminate one or more sub-operations 100, thereby accelerating one or more of the operation times. For example, in one of the sub-operations 100 at a particular target frequency, the signal at that particular target frequency may be transmitted a single time instead of transmitted multiple times. Any technique(s) for achieving the desired operation times can be implemented.

However, in one embodiment, when multiple frequency sweeps are implemented, it is preferred that the blocks of operation times of the frequency steps at each target frequency in each frequency sweep match each other. For example, assuming first and second frequency sweeps, the frequency sweeps can be controlled to achieve the following:

TABLE 1

| | Frequency Sweep 1 | | | Frequency Sweep 2 | |
|---|---|---|---|---|---|
| Step | Target Frequency | Operation time (µs) | Step | Target Frequency | Operation time (µs) |
| 1 | F1 | 30 | 1 | F1 | 30 |
| 2 | F2 | 30 | 2 | F2 | 30 |
| 3 | F3 | 40 | 3 | F3 | 40 |
| . | . | . | . | . | . |
| . | . | . | . | . | . |
| N | Fn | 50 | n | Fn | 50 |

As indicated in Table 1, some of the operation times within the two frequency sweeps are shown as being different from one another. However, it may be preferred that the frequency sweeps are controlled such that the same steps in each frequency sweep have the same operation times. For example, step 1 in each of frequency sweep 1 and frequency sweep 2 at the target frequency F1 have the same operation time; step 2 in each of frequency sweep 1 and frequency sweep 2 at the target frequency F2 have the same operation time; etc. This described control helps to ensure that the two frequency sweeps are performed as close to identically as possible so that the resulting return signals from each frequency sweep can be obtained under as close to identical conditions as possible, which helps when comparing and analyzing the resulting return signals from the frequency sweeps so that an apples-to-apples comparison between the two frequency sweeps can be performed. Although Table 1 shows two frequency sweeps, a larger number of frequency sweeps can be performed, and each frequency sweep can be controlled in the manner described with respect to frequency sweeps 1 and 2.

Each frequency sweep need not encompass the same frequency range. For example, one frequency sweep can have a start frequency Fs1 and an end frequency Fe2, while a second frequency sweep can have a start frequency Fs3 and an end frequency Fe4. Fs1 can be equal to, less than or greater than Fs3, and Fe2 can be less than, equal to, or greater than Fe4. However, the frequency sweeps should have at least some overlapping frequency range with one another, where in the overlapping range the frequency sweeps are controlled as described above and in Table 1 so that the frequency steps in the overlapping range in each frequency sweep are the same and the operation times of the frequency steps in the overlapping range are identical to one another (i.e. as indicated in Table 1 above, in the overlapping range, the operation times of the first frequency steps of the first frequency sweep are identical to the corresponding operation times of the second frequency steps of the second frequency sweep). However, as explained above, in one embodiment, in the overlapping range, the operation times of at least some of the first frequency steps of the first frequency range may not be equal to one another, and the operation times of at least some of the second frequency steps of the second frequency range may not be equal to one another. In another embodiment, in the overlapping range or across the entire range of each frequency sweep, the operation times of the frequency steps in one of the frequency sweeps may be equal to one another, and the operation times of the frequency steps in the other frequency sweep may be equal to one another.

The frequency sweeps described herein may occur in succession one after the other in a relatively short overall timeframe. In another embodiment, the frequency sweeps described herein do not occur in succession but are instead spaced from one another over a relatively long time period. For example, one frequency sweep can occur on one day and another frequency sweep can occur on a different day.

In another embodiment, instead of implementing multiple frequency sweeps, a single frequency sweep can be implemented. In the single frequency sweep, the blocks of operation time may be the same as one another or some of the blocks of operation time may differ from one another.

In another embodiment, a non-invasive sensor can include aspects of both of the sensors 5, 50. For example, a sensor can include both two or more antennas as described herein as well as two or more of the LEDs described herein. The antennas and the LEDs can be used together to detect an analyte. In another embodiment, the antennas can be used to perform a primary detection while the LEDs can confirm the primary detection by the antennas. In another embodiment, the LEDs can be used to perform a primary detection while the antennas can be used to confirm the primary detection by the LEDs. In another embodiment, the antennas (or the LEDs) can be used to calibrate the sensor while the LEDs (or the antennas) can perform the sensing.

The terminology used in this specification is intended to describe particular embodiments and is not intended to be limiting. The terms "a," "an," and "the" include the plural forms as well, unless clearly indicated otherwise. The terms "comprises" and/or "comprising," when used in this specification, specify the presence of the stated features, integers, steps, operations, elements, and/or components, but do not preclude the presence or addition of one or more other features, integers, steps, operations, elements, and/or components.

The examples disclosed in this application are to be considered in all respects as illustrative and not limitative. The scope of the invention is indicated by the appended claims rather than by the foregoing description; and all changes which come within the meaning and range of equivalency of the claims are intended to be embraced therein.

The invention claimed is:

1. A sensor system, comprising:
a detector array having at least one transmit element and at least one receive element, the at least one transmit element is positioned and arranged to transmit a transmit signal into a target, and the at least one receive element is positioned and arranged to detect a response resulting from transmission of the transmit signal by the at least one transmit element into the target;
a transmit circuit that is electrically connectable to the at least one transmit element, the transmit circuit is configured to generate the transmit signal to be transmitted by the at least one transmit element, the transmit signal is in a radio frequency or visible range of the electromagnetic spectrum;
a receive circuit that is electrically connectable to the at least one receive element, the receive circuit is configured to receive the response detected by the at least one receive element; and
a control system connected to the transmit circuit and configured to implement at least first and second frequency sweeps by the at least one transmit element, the first frequency sweep occurs over a first frequency range from a start frequency to an end frequency, the second frequency sweep occurs over a second frequency range from a start frequency to an end frequency, and the first frequency range and the second frequency range overlap one another;
the first frequency range and the second frequency range where they overlap have first frequency steps and second frequency steps, respectively; the first frequency steps are the same as the second frequency steps; each frequency step of the first frequency steps and the second frequency steps has an associated operation time, and the operation times of the first frequency steps are identical to the operation times of the second frequency steps;
the at least one transmit element and the at least one receive element comprise antennas, and the first frequency range and the second frequency range are each in a radio or microwave frequency range of the electromagnetic spectrum.

2. The sensor system of claim 1, wherein the operation times of at least some of the first frequency steps are not equal to one another, and the operation times of at least some of the second frequency steps are not equal to one another.

3. The sensor system of claim 1, wherein the operation times of the first frequency steps are equal to one another, and the operation times of the second frequency steps are equal to one another.

4. The sensor system of claim 1, wherein each operation time includes a plurality of sub-operations.

5. The sensor system of claim 4, wherein the plurality of sub-operations of at least one of the operation times include a plurality of transmissions of a frequency by the at least one transmit element.

6. The sensor system of claim 1, wherein the detector array, the transmit circuit, the receive circuit, and the control system are incorporated into a wearable watch or a tabletop device.

7. The sensor system of claim 1, wherein the target is a body fluid, and the sensor system is configured to sense blood glucose, blood alcohol, white blood cells, or luteinizing hormone.

8. A method of operating a sensor system that includes a detector array having at least one transmit element and at least one receive element, the at least one transmit element is positioned and arranged to transmit a transmit signal into a target, and the at least one receive element is positioned and arranged to detect a response resulting from transmission of the transmit signal by the at least one transmit element into the target, a transmit circuit that is electrically connectable to the at least one transmit element where the transmit circuit is configured to generate the transmit signal to be transmitted by the at least one transmit element, the transmit signal is in a radio frequency or visible range of the electromagnetic spectrum, and a receive circuit that is electrically connectable to the at least one receive element where the receive circuit is configured to receive a response detected by the at least one receive element, the method comprising:

controlling the sensor system to implement at least a first frequency sweep and a second frequency sweep by the at least one transmit element, the first frequency sweep occurs over a first frequency range from a start frequency to an end frequency, the second frequency sweep occurs over a second frequency range from a start frequency to an end frequency, and the first frequency range and the second frequency range overlap one another, the first frequency range and the second frequency range where they overlap have first frequency steps and second frequency steps, respectively; the first frequency steps are the same as the second frequency steps; each frequency step of the first frequency steps and the second frequency steps has an associated operation time, and the operation times of the first frequency steps are identical to the operation times of the second frequency steps, wherein the at least one transmit element and the at least one receive element comprise antennas, and the first frequency range and the second frequency range are each in a radio or microwave frequency range of the electromagnetic spectrum.

9. The method of claim 8, comprising controlling the sensor system so that the operation times of at least some of the first frequency steps are not equal to one another, and the operation times of at least some of the second frequency steps are not equal to one another.

10. The method of claim 8, comprising controlling the sensor system so that the operation times of the first frequency steps are equal to one another, and the operation times of the second frequency steps are equal to one another.

11. The method of claim 8, comprising controlling the sensor system so that each operation time includes a plurality of sub-operations.

12. The method of claim 11, comprising controlling the sensor system so that the plurality of sub-operations of at least one of the operation times include a plurality of transmissions of a frequency by the at least one transmit element.

13. The method of claim 8, wherein the detector array, the transmit circuit, the receive circuit, and the control system are incorporated into a wearable watch or a tabletop device.

14. The method of claim 8, wherein the target is a body fluid, and the sensor system is configured to sense blood glucose, blood alcohol, white blood cells, or luteinizing hormone.

\* \* \* \* \*